(12) United States Patent
French et al.

(10) Patent No.: US 10,925,810 B2
(45) Date of Patent: Feb. 23, 2021

(54) METHOD AND SYSTEM FOR IMPROVING AND ASSISTING IN MEDICATION COMPLIANCE

(71) Applicant: EMME, Inc., San Francisco, CA (US)

(72) Inventors: Amanda B French, San Francisco, CA (US); Janene Fuerch, Los Altos, CA (US); Craig Nichols, Carrboro, NC (US)

(73) Assignee: EMME, Inc., San Francisco, CA (US)

( * ) Notice: Subject to any disclaimer, the term of this patent is extended or adjusted under 35 U.S.C. 154(b) by 0 days.

(21) Appl. No.: 15/950,059

(22) Filed: Apr. 10, 2018

(65) Prior Publication Data

US 2018/0289591 A1 Oct. 11, 2018

Related U.S. Application Data

(60) Provisional application No. 62/483,475, filed on Apr. 10, 2017.

(51) Int. Cl.
| | |
|---|---|
| *A61J 7/04* | (2006.01) |
| *G16H 20/10* | (2018.01) |
| *A61J 7/00* | (2006.01) |
| *A61J 1/03* | (2006.01) |
| *G16H 50/70* | (2018.01) |
| *G16H 40/67* | (2018.01) |
| *G16H 20/13* | (2018.01) |

(52) U.S. Cl.
CPC ............ *A61J 7/0481* (2013.01); *A61J 7/0076* (2013.01); *A61J 7/0418* (2015.05); *A61J 7/0436* (2015.05); *G16H 20/10* (2018.01); *A61J 1/035* (2013.01); *A61J 7/0454* (2015.05); *A61J 2200/30* (2013.01); *A61J 2205/70* (2013.01); *G16H 20/13* (2018.01); *G16H 40/67* (2018.01); *G16H 50/70* (2018.01)

(58) Field of Classification Search
CPC ......... A61J 1/035; A61J 2200/30; A61J 7/04; A61J 7/0418; A61J 7/0436; A61J 7/0445; B65D 83/0463; G06F 19/3462
See application file for complete search history.

(56) References Cited

U.S. PATENT DOCUMENTS

| | | | | |
|---|---|---|---|---|
| 2013/0195326 A1* | 8/2013 | Bear | ................... | G06F 19/3456 382/128 |
| 2013/0319902 A1* | 12/2013 | Tufi | ....................... | A61J 1/035 206/534 |
| 2016/0354283 A1* | 12/2016 | Cho | ......................... | A61J 7/02 |

* cited by examiner

*Primary Examiner* — Omeed Alizada
(74) *Attorney, Agent, or Firm* — Wilson Sonsini Goodrich & Rosati

(57) ABSTRACT

A medication adherence system for facilitating adherence to a medication dosage schedule is provided, comprising a smart case to receive or adhere to a medication pack, a sensor for detecting a medication event, and a tangible computer readable medium interface for users to obtain feedback regarding their adherence to their respective medication dosage schedules.

16 Claims, 9 Drawing Sheets

METHOD AND SYSTEM FOR IMPROVING AND ASSISTING IN MEDICATION COMPLIANCE

RELATED APPLICATION

This application claims priority and other benefits from U.S. Provisional Patent Application Ser. No. 62/483,475, filed Apr. 10, 2017, entitled "Method and System For Improving Medication Compliance." Its entire content is specifically incorporated herein by reference.

FIELD OF THE INVENTION

This invention relates generally to medical devices and more particularly to systems and methods for ensuring compliance by a patient in taking scheduled medications.

BACKGROUND

One of the most significant problems that negatively impacts the effectiveness of medications is poor patient adherence—in other words, patients' inability or unwillingness to take their medications as prescribed. For medications to work effectively, they must be taken at very specific doses and time intervals. When patients deviate from the prescribed medication regimen, or fail to take a dose they often render their medications less effective or completely ineffective and, even worse, they may experience adverse effects from their improperly or irregularly used medications.

Healthcare providers and healthcare systems recognize the problem of poor medication adherence, but there is still enormous potential for improvement. There is a need for systems to assist patients and users in medication compliance by providing them with real-time, periodic compliance or non-compliance indicators and signals through various auditory, visual or other stimuli.

SUMMARY

The present application provides a smart case, which is a medication compliance device, for holding a medication pack having a plurality of medication dose holders each configured to hold a single medication dose. The smart case is configured to wirelessly communicate with an external device to monitor compliance, send reminders, predict effectiveness of the medication based on the actual dosing schedule recorded by the system, and the like.

In a first aspect of the present invention, the smart case comprises a base shell for removably receiving a medication pack, a lid attached to the shell and having a closed position where the medication pack is covered and open position where the medication dose holders on the medication pack are accessible by a user, and a lid sensor configured to detect when the lid is moved between the closed position and the open position. The smart case further includes circuitry comprising a processor and a wireless link, wherein the lid sensor is connected to the circuitry a power source connected to the circuitry. The circuitry is configured to emit a signal via the wireless link to the external device when the cover is opened.

In specific embodiments, the lid may be attached to the base by a hinge and the base may comprise a lid sensor that detects when the lid opens. In other embodiments, the lid may be slidably attached to the base and the base comprises a lid sensor that detects when the lid is slid to an open position. In still other embodiments, the smart case may further comprise a medication pack sensor which detects when the medication pack is accessed from the smart case, wherein the lid sensor is connected to the circuitry and the circuitry is configured to emit a signal via the wireless link to the external device each time a medication pack is accessed. In still other embodiments, the smart case may further comprise a dose holder sensor which detects opening of a single dose holder, wherein the lid sensor is connected to the circuitry and the circuitry is configured to emit a signal via the wireless link to the external device each time a dose holder is opened. The medication pack sensor and dose holder sensor may comprise any one or more of a variety of sensors, such as capacitive, resistive, electromagnetic (e.g., Hall Effect), optical (e.g., infrared), inductive, mechanical switches, acoustic (e.g., microphones), or image processing sensors. The circuitry may be configured to power the medication pack sensor or dose holder sensor only when the lid sensor indicated that the lid is open. In still further embodiments, the smart case may further comprise a frame attached to the base for removably receiving the medication pack, and the frame may be attached to the base by an attachment mechanism that raises the frame and medication pack above an upper surface of the base when the lid is opened. For example, the attachment mechanism may comprise a spring hinge.

In a second aspect of the present invention, a method for facilitating compliance with a medication dosage schedule comprises sensing, with a processor on a medication compliance device such as the smart case coupled with a medication pack, when a user has interacted with the medication pack to gain access to individual medication holders on the medication pack. The processor on the medication compliance device determines whether a medication pack has been accessed, or an individual medication dose has been removed from an individual medication dose holder on the medication pack and transmits the time that either of these events occurred to an external device for recording or determining compliance with the medication dosage schedule. A user is determined to be in compliance with the medication dosage schedule, if all medication events, i.e. consumption of medication doses, occurred in accordance to an indicated, recommended and/or preset schedule within a given medication window. A user is determined not to be in compliance with the medication dosage schedule, if one or more medication events did not occur within a given medication window, as scheduled. If a user is determined not to be in compliance, feedback in form of various stimuli is provided to the user in order to inform the user and to encourage adherence to the medication dosage schedule. If the medication in question is an oral contraceptive pill, such feedback may include instructions on how to proceed if the user is determined not to be in compliance and if the user is at a certain risk of pregnancy.

In specific embodiments of such methods, sensing user interaction with the medication pack is detected by a first sensor on the medication compliance device and sensing when the individual medication dose has been removed from the individual medication dose holder on the medication pack is detected by a second sensor on the medication compliance device. The first sensor is typically active at all times, but the second sensor is energized to be in a sensing mode only after the first sensor detects user interaction with the medication pack. In this way, battery life of the medication compliance device can be extended, particularly when the second sensor is an audible, optical or other high energy usage sensor.

In a third aspect of the present invention, a medication adherence system communicates the sensing of user interaction with the medication pack contained within the smart case via a network that may be accessible by or share the sensed data with a third party such as a health care provider to whom the user has granted permission to receive such data. The medication adherence system may include an application server which may reside in a mobile phone, or may reside in any centralized server or computer that is accessible via a network. The application server may contain a software application and a database.

DETAILED DESCRIPTION

Before the present systems and methods are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

As used herein, the terms medication and pill may be singular or plural, can be used interchangeably herein, and refer to any size or shape of a solid formulation that is prepared for oral administration such as a pill, capsule, tablet, granule, and so forth. Furthermore, as used herein, the terms medication and pill may refer to prescription as well as over-the-counter medications as well as dietary supplements including vitamins and minerals. Furthermore, the terms blister pack and medication pack may be used interchangeably herein. In a preferred embodiment, the terms medication, medicine, and pill refer to a prescription contraceptive medication. In addition, the terms medication and pill refer to any orally administered formulation which need to be used on a predetermined, scheduled basis.

A medication event, as used herein, may include, but is not limited to, the user interacting with their medication, the user accessing the medication pack from the smart case, the dispensing of medication from a medication pack or medication dose holder, or the user opening and closing the case which contains the medication doses in the medication dose holders.

The embodiments of the present invention are generally directed to systems and methods for assistance in medication compliance in users or patients who are undergoing prescription or over-the-counter medication therapy, and also for assistance to any user of dietary supplements including vitamins and minerals.

In various embodiments, the present invention is directed toward a medication adherence system including a smart case, which is a medication compliance device, and a method for assisting a user or patient in medication compliance and for facilitating adherence to a medication dosage schedule.

Figure 1:
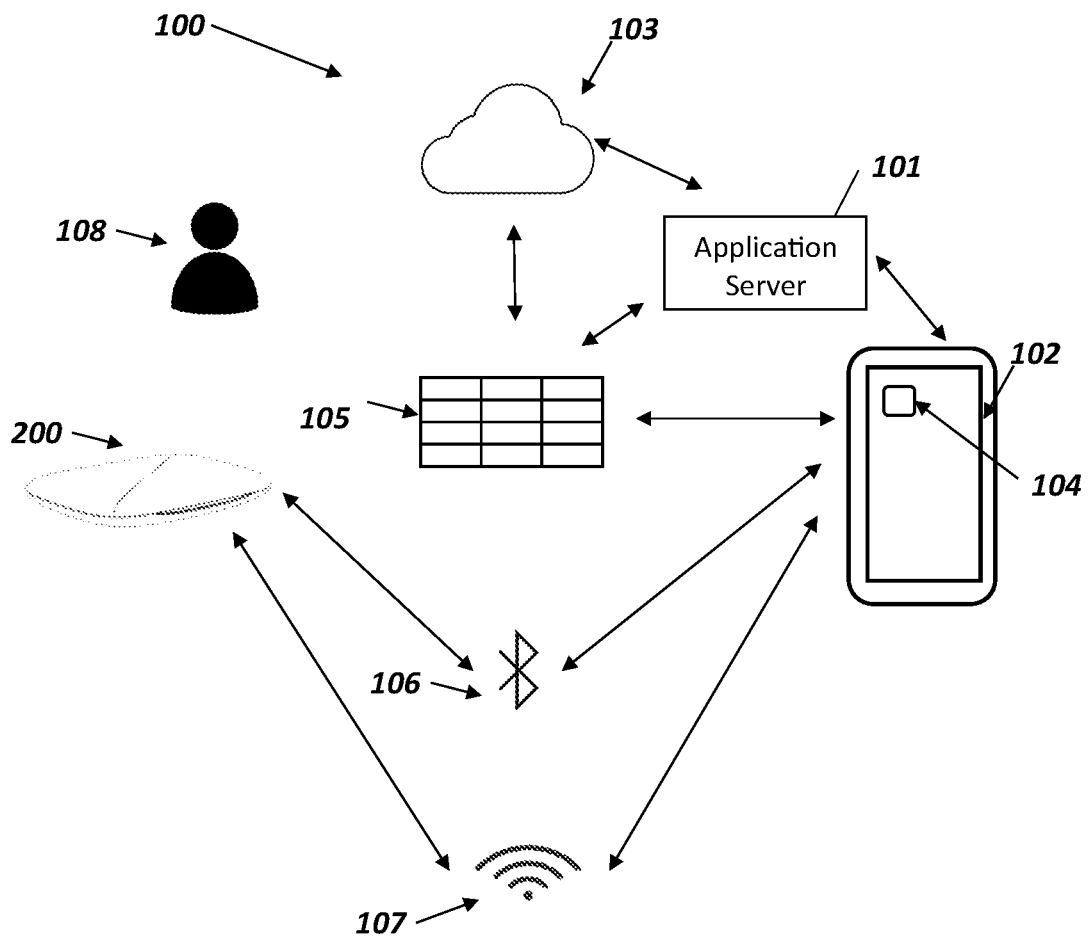
FIG. 1 illustrates an embodiment of the medication adherence system.

With reference to FIG. 1, the medication adherence system 100 may include an application server 101 which may reside in a mobile phone 102, or may reside in any centralized server or computer that is accessible via a network. In one example, the application server may reside in a cloud server 103. The application server may contain a software application 104 and a database 105. The database 105 may include such information as compliance data, prescription data, and analytics on user behaviour.

The medication adherence system 100 may also include a sensor and data-enabled smart case 200. The smart case 200 can be connected with the application server 101 via Bluetooth 106, wi-fi 107, or another data transmission modality. The application server 101 is preferably connected to a mobile phone 102 which can be defined as any mobile phone capable of communicating with the smart case 200 and running the software application 104. For example, the mobile phone 102 could be an Apple iPhone, an Android phone, a Samsung Galaxy phone, or another mobile device that has cellular network capability such as a 3G or 4G version of the Apple iPad or another tablet.

Figure 2A:
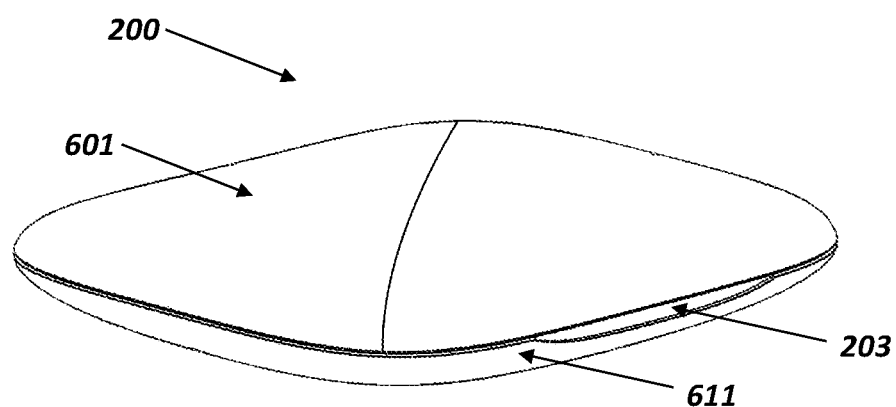
FIG. 2A depicts an embodiment of the smart case in a closed position.
Figure 2B:
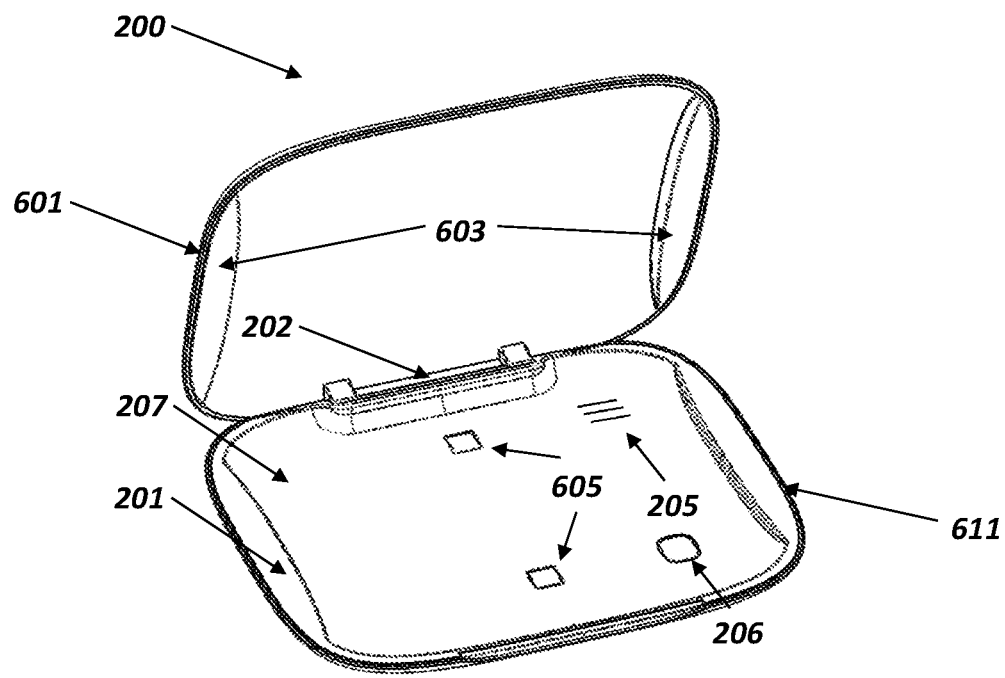
FIG. 2B depicts an embodiment of the smart case in an open position.
Figure 3:
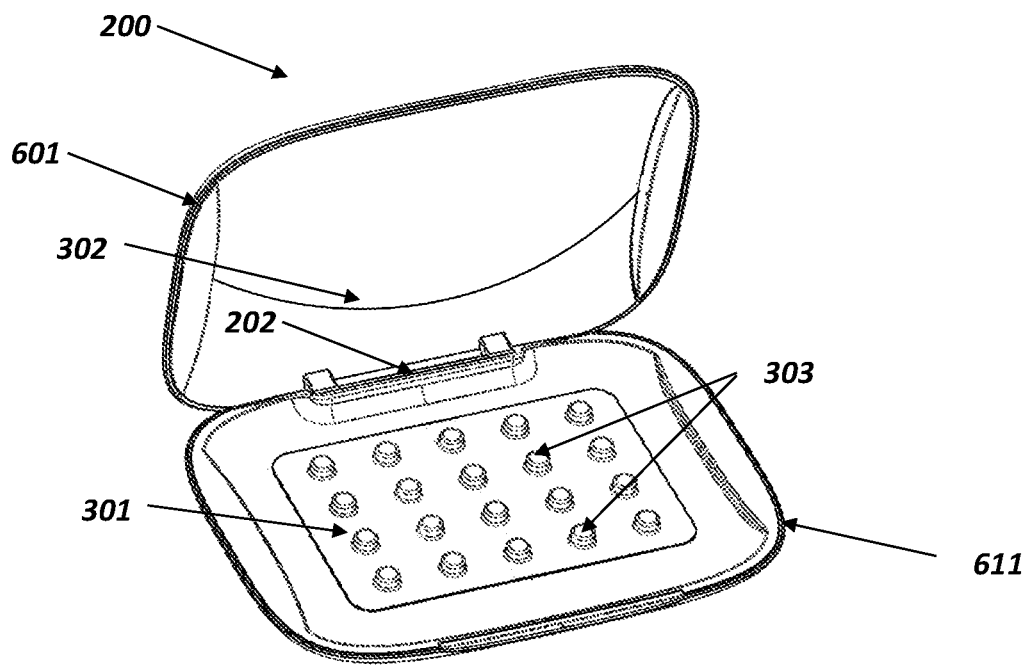
FIG. 3 depicts an embodiment of the smart case in an open position with a medication pack removably attached and an additional pocket.

In various illustrative embodiments of the invention, the smart case 200, as shown in FIG. 2A, includes a lid 601 and a base 611, and may be joined by a hinge 202, as shown in FIG. 2B. The base includes a receptacle 207 which is configured to receive a plurality of medication dose holders 303, such as individual blisters in a medication pack such as a blister pack 301, each of which typically includes a single dose of a medication, usually a pill, capsule, lozenge, or the like. The medication dose holders 303 are configured so that a user can open one at a time to access the medication dose therein, usually according to a predetermined dosing schedule, e.g. daily. The lid 601 and base 611 each have inner and outer surfaces and can be opened and closed. The lid may be held closed by magnets 602 or other conventional latches. The lid and base may be fabricated from any durable, lightweight material that is suitable to protect a plurality of medication doses from light, temperature, and other ambient influences. The smart case 200 dimensions would be derived to accommodate a variety of medication packs 301. For example, the dimensions of a medication pack receptacle 207 (see FIG. 2B) could range from a length of approximately 50-65 mm and a width of approximately 65-100 mm. The smart case, as shown in FIG. 3, may further include a compartment 302 for storing other materials and products, such as alternative birth control methods (condoms etc).

Figure 4:
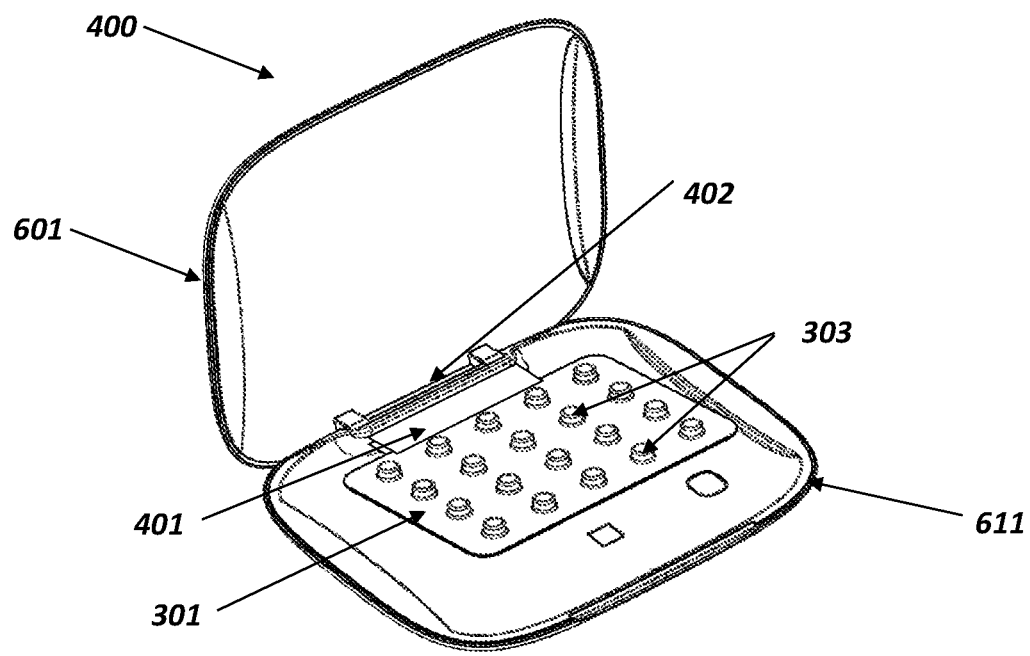
FIG. 4 depicts an embodiment of the smart case in an open position wherein a medication pack is removably attached to a frame.

As shown in FIG. 4, an embodiment of a smart case 400 includes a lid 601 and base 611 as described previously and can be connected with a hinge 402 at their inner and/or outer surfaces. The hinge can accommodate a frame 401 that is attached to the base for removably receiving a medication pack 301, whereby the attachment mechanism for the frame 401 can be configured to comprise a spring hinge, and adapted to urge the medication pack 301 which contains a plurality of medication doses, such as pills 303, forwards or upwards to facilitate dispensing of one or more medication doses.

Figure 5:
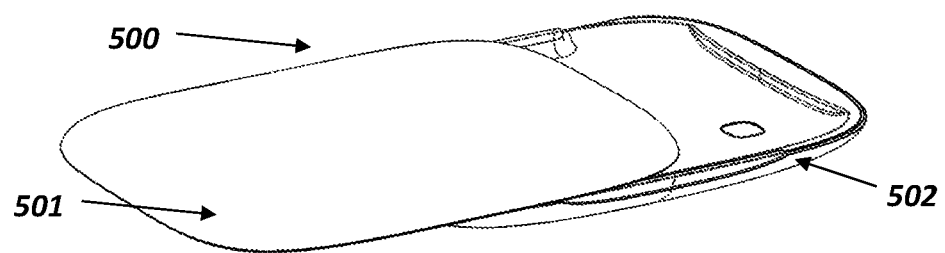
FIG. 5 depicts an embodiment of the smart case in an open position with a sliding open/close mechanism.

In another embodiment of the present invention, a smart case 500, as shown in FIG. 5, comprises a case lid 501 which slides open and closed over a case base 502 to expose the medication pack 301. Other embodiments of the smart case can take the form of a sheath, sleeve, pill bottle, or any other form of container which can accept the plurality of medication dose holders and doses.

Figure 6:
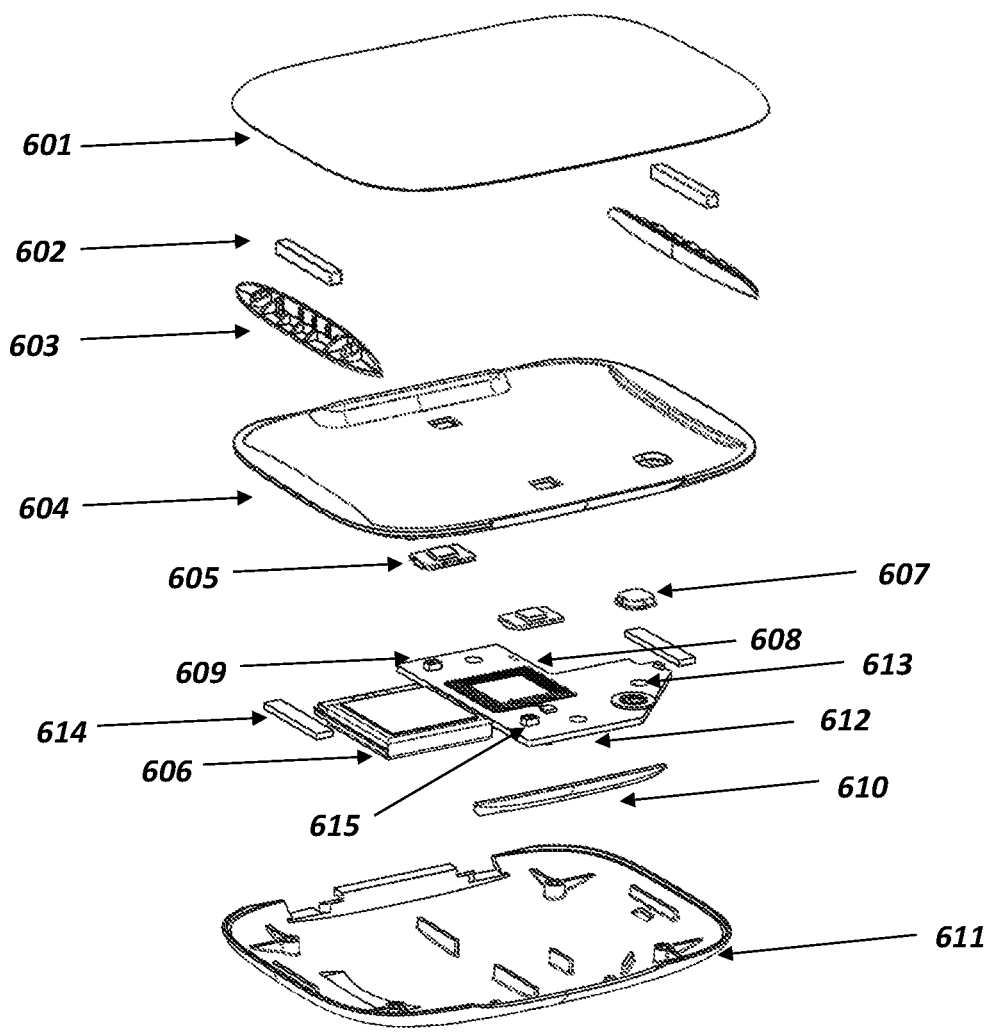
FIG. 6 illustrates an embodiment of the smart case in an exploded view.

FIG. 6 shows an example of a smart case in an exploded view. The smart case 200 contains at least one sensor that is operatively connected to the circuit board 609 of the smart case 200 and can sense when the smart case 200 is opened and closed. In one embodiment, this sensor is a Hall Effect sensor 613 which functions based on a change in the magnetic field detected between a magnet 602 and steel bar 614 which alternatively could also be a magnet. The magnet 602 is secured to the lid 601 of the smart case 200 via magnet covers 603. This sensor could be sufficient for detecting a medication event, especially when paired with a computer-aided algorithm which can determine the relevance of the signal from each sensor.

Alternatively, the signal detection by a sensor such as the Hall Effect sensor 613 could trigger a secondary set of sensors which detect the status of the blister pack 301 in the smart case 200. In the one embodiment, this is achieved by an inductive sensor 608 which can detect when the blister pack 301 is removed from the smart case 200. Alternatively, this could be achieved by infrared (IR) sensors 615 which can monitor the presence or absence of individual medication doses 303 or the medication pack 301 through the IR window 605. Audio data could also be monitored and collected through an audio port 205 on the smart case 200. The duration and quality of any of the signals sensed by the smart case can be interpreted and analyzed as a potential medication event.

The electrical activity is supported by a power unit 606. The data is transmitted via low energy Bluetooth 106 to the software application 104, and can also be stored and processed in a chip on the circuit board 609. The pairing between the software application 104 and the smart case 200 can be triggered by a switch, which is activated by the user by depressing the button 607 relative to the midframe 604 of the smart case 200.

The smart case 200 can utilize a variety of sensors for detecting opening and/or closing of the lid 601 or 501 and for removing individual medication doses 303 on a medication pack 301. A presence sensor, e.g., an optical, pressure or conductivity sensor, detects the presence or absence of, e.g., a medication dose, by detecting the electrical continuity or discontinuity between two sensors. Electromechanical sensors sense a change in magnetic or solid state electronic fields. Audio sensors, such as microphones, are able to detect sounds produced by or near the medication adherence system, e.g. by opening or closing the lid 601, by removing individual medication doses 303, etc. Sensors inside and/or outside of the smart case can track ambient conditions such as temperature, humidity, ambient light.

The smart case 200 may also have a light-emitting diode (LED), which is viewed by the user through a light pipe 610. Multi-color or single color LEDs may be used to convey information to users in accordance to color. For example, the light source may turn red when a user is overdue in taking a medication dose, and the medication is a contraceptive pill, and as a consequence the user is at a heightened risk of pregnancy. The light source may turn green when the medication dose was taken in accordance to the indicated or recommended dosage schedule, and as a consequence the user faces no or only a low risk of pregnancy. The light source may turn yellow when the medication dose was taken later than indicated by the dosage schedule, and as a consequence the user is at a medium risk of pregnancy. The light source may turn blue when a network connection is established and information is received and /or transmitted. The light sources may be piped around the surfaces of the smart case and therefore be visible from all sides; or it may be a one-sided light pipe 203, as shown in FIG. 2A. The circuit board 609 is secured in the smart case 200 between the base 611 and a midframe 604, as shown in FIG. 6. Such a subassembly may be attached to the lid 601 of the smart case 200.

Figure 7:
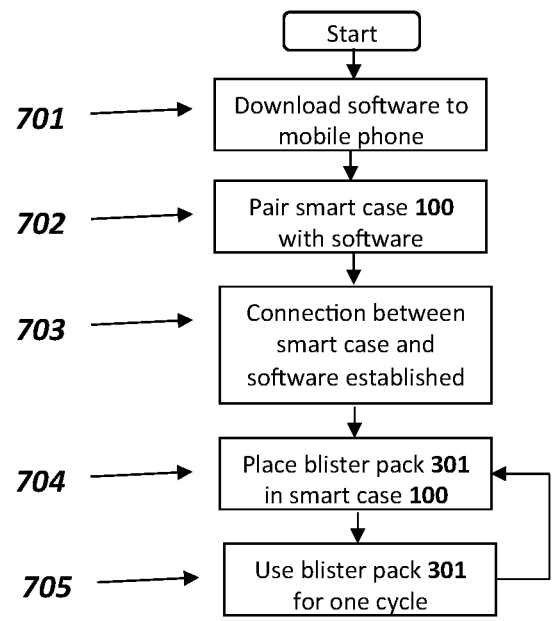
FIG. 7 illustrates an exemplary set-up operation of the method for facilitating compliance with a medication dosage schedule.

FIG. 7 illustrates an exemplary set-up operation of the method for facilitating compliance with a medication dosage schedule within the medication adherence system. At a step 701 a user 108 will download the software application 104 to their mobile phone 102. At a step 702 the user 108 can pair the smart case 200 with the software application 104 by entering pairing mode on the software application 104. The activation of a switch on the smart case 200 (for example, by depressing the button 206) puts the smart case 200 in pairing mode. At a step 703, once paired via Bluetooth 106, for example, the connection between the smart case 200 and software application 104 is maintained. The smart case 200 may be received by the user 108 with a medication pack 301 already stored in it, or, at a step 704, the user 108 may place the medication pack 301 into the smart case 200. At a step 705, at the beginning of each new cycle, the user 108 places a new medication pack 301 into the smart case 200.

Figure 8:
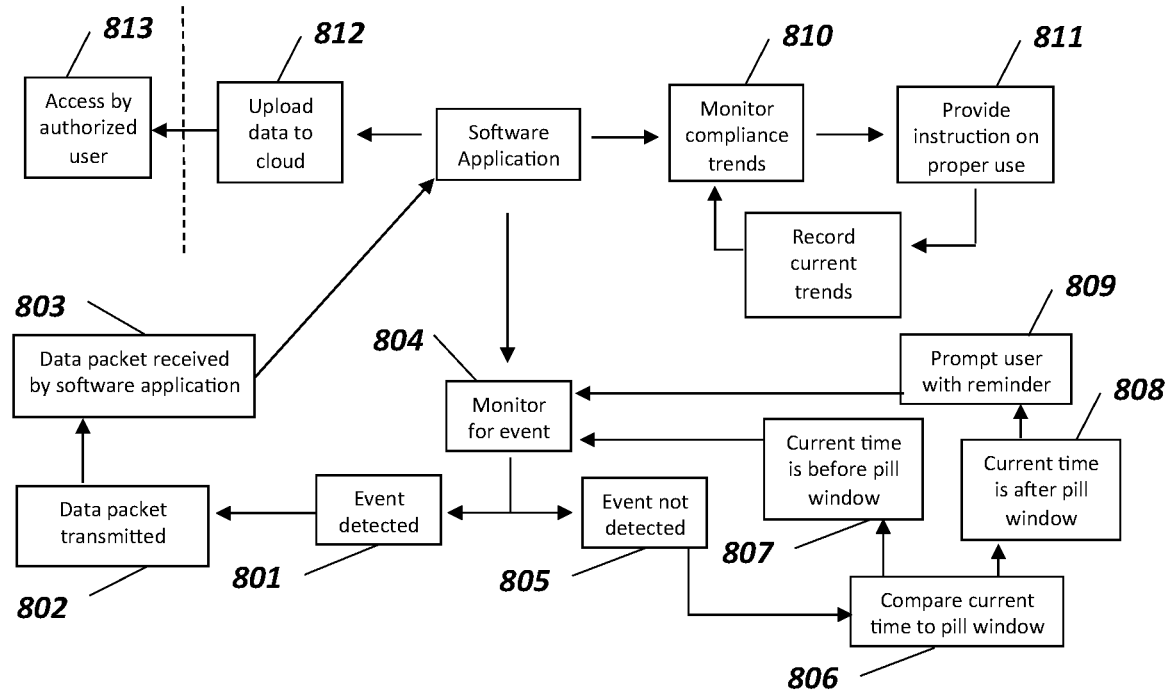
FIG. 8 illustrates an exemplary operation of the medication adherence system.

FIG. 8 illustrates an exemplary operation of the medication adherence system. The diagram illustrates exemplary event detections and data transmissions for monitoring a user's interactions with the smart case, facilitating dose reminders, logging the compliance status, and providing instructions such as indicating the current risk of pregnancy and steps to take in order to avoid pregnancy such as using alternative contraceptive methods, if the medication is a contraceptive pill. At a step 801, the sensors on the smart case 200 detect when the smart case 200 is opened and may detect when the medication pack 301 is removed from the smart case 200 and/or an individual medication dose holder 303 is opened and/or the individual medication dose is removed and presumably consumed. At a step 802, sensing data will be transmitted until a step 803 in which the data is received by the software application 104 on the mobile phone 102. The sensing data may be stored on a local processor on the smart case 200 until the case is within range of the mobile phone 102.

At a step 804, the mobile phone 102 software application 104 monitors the data that it receives from the smart case 200 relative to the indicated or recommended dosage schedule, i.e., the time on each day when the user 108 is expected or due to take one or more medication doses. At a step 805, a missed dose is noticed by the mobile phone 102 software application 104 as indicated by an absence of data sent from the smart case 200. At a step 806, the current time is compared to a "medication window", i.e. the time window during which the user 108 is supposed to take one or more medication doses 303. The mobile phone 102 software application 104 accounts for time zone changes when the user 108 is traveling to accurately make this assessment. At a step 807, if the current time is before the medication window, the medication adherence system 100 continues to passively monitor. At a step 808, the current time is evaluated to be past the medication window. In this case, at a step 809 the mobile phone 102 software application 104 prompts the user 108 with a reminder, for example via a SMS text message, local notification, or push notification. The software application 104 continues to send reminders until the user 108 consumes one or more medication doses 303 as indicated by the appropriate medication dosage schedule. At a step 810, the software application 104 categorizes the data it receives from the smart case 200 to determine if the medication dose was taken early, on time, late, or if the medication window was entirely missed. At a step 811, this information is interpreted in order to provide the user 108 with clear and relevant instructions for how to properly use the medication and, e.g., reduce pregnancy risk. At a step 812, this data can be uploaded to the cloud 903. At a step 813, this database 105 can be shared with an authorized user such as a pharmacy or other health care provider, who can use the information to provide informed recommendations to the user 108 on medication selection and management if a medication dose was missed.

Motion sensors data can be generated by a sensor attached to the lid 601 and/or base 611 of the smart case 200, as shown in FIG. 6. The data collected by the motion sensor can indicate when the smart case 200 is moved, a lid 601 is opened, when the frame 401 is pushed up or down, and any other movements including vibrations or a change in pressure results that may occur when a medication dose 303 is dispensed from the smart case 200. For example, the hinge 202 can accommodate a sensor that is configured to sense the opening and/or closing (motion) of the lid 601 or base 611. The motion data can be analysed to determine whether it matches with a distinctive movement pattern that is associated with dispensing a medication dose and whether, in accordance with the movement pattern, a medication was likely dispensed from the smart case 200.

In some embodiments, the case may generate a wireless signal via wi-fi 107, Bluetooth 106, or Bluetooth 106 low energy to send the sensor data to the application server 101. For users 108 who are mobile with the smart case 200, low energy Bluetooth is the preferred embodiment.

The medication adherence system may further comprise a power unit 606. Power to the smart case 200 and the medication adherence system 100 is provided by either a battery or a power supply module which connects to an outside power source. Power can, e.g., be provided through a standard universal serial bus (USB) port. Additionally or alternatively, other ports may be used that support proprietary connectors, micro-USB, SATA cables, Lightning, etc.

The software application 104 can be programmed with an algorithm to track a user's medication compliance, i.e. adherence to a medication dosage schedule, by comparing the most recent medication dispensing event, such as opening of the case, to a pre-programmed "ideal" schedule of medication dispensing events. Alarms, reminders and other feedback can then be provided using a visual output, auditory output or tactile output to alert the user to proceed with a medication dispensing event or to provide the user with instructions what else to do, if a medication dose was missed. The smart case 200 may generate a signal such as light, voice, vibration, or a combination thereof, to assist the user in adhering to a medication dosage schedule. The signal may be generated in predefined, periodic time increments or intervals, or may only be generated if a medication dose was not dispensed as scheduled.

Additionally, indicators may be present on the smart case to prompt the user to initiate a medication event, or to indicate that a medication event has occurred. Indicators that may be included on the smart case can comprise visual indicators (e.g. LED light and/or array, electroluminescent display, electronic paper, color changing components, etc.), olfactory indicators, and tactile indicators (e.g. vibration, raised features). For example, a visual indicator may communicate the time and location of the most recent medication event, or the medication window for the next medication event.

The medication adherence system may further comprise a communication module configured to permit communication with an external smart device such as mobile phones, smart phones, tables, portable media devices, wearable devices, laptops, servers using a data transmission protocol such as RFID, Bluetooth, NFC, sigFox, qual2 or similar. The external device may include a piece of software, e.g. a mobile application, that can receive and process sensor data, and generate a user interface for various users to share the sensor data and/or its interpretation.

The external device can be used to display reminders, compliance summaries or other information such as advice on what to do if a medication event was missed. In another embodiment, the smart case is configured to permit wireless or wired communication to a health network or medical professional in accordance to the user's pre-recorded instructions.

The connection allows information, e.g. sensor data, recorded by the electronic display, user input, and sensors, e.g. audio sensor/motion sensor/lid sensor/pressure sensor, to be transmitted electronically across a network. One or more networks can be used to communicatively couple the various components of the medication adherence system. A network connection can also be established with physicians, pharmacists and other providers to share the sensed data with.

Generally, the communication module establishes a wired or wireless connection between the case and other computing devices. For example, the information may be transmitted via wireless connection, if any antenna technology is supported such as Bluetooth, Bluetooth Low Energy (BLE), cellular (3G, 4G, etc.), Near Field Communication (NFC), wireless local area network (WLAN) transmitters, Infrared, V-2-V communication, radiofrequency (RF), and other wireless technologies. The information may also be transmitted via wired connection using, e.g., a USB or mini-USB port.

The communication module can be housed within an electronics module compartment which may also house additional modules and/or components such as processors, communication devices, integrated electronics, memory storage devices, batteries, sensors.

For oral contraceptives used for birth control, there is often a predetermined dosing regimen for how to proceed if an oral contraceptive pill is missed. This predetermined dosing schedule is based on what time the pill 303 was missed in the medication dosing window (e.g. @7 PM vs. 5 PM—2 hours later than daily dosing window), when the pill was missed in the overall cycle (e.g. day 7 of a 28 day cycle), what type of birth control a user is prescribed (e.g. combined hormonal, or progesterone only), and other factors. In some embodiments, smart case 200 will have the ability to display different stimuli to the user to communicate different treatment recommendations (e.g. via various LED configurations).

Medication events may be recorded via a number of different means. In one embodiment, a latching mechanism on the smart case 200 can record when the latch is opened or closed, such as via an electrical switching mechanism (e.g. circuit completed or broken when case is opened/ closed), a mechanical mechanism (e.g. a sensor is depressed when the smart case is closed only when a medication pack is present within the case), a piezo electric mechanism, or an optical mechanism. In another embodiment, pressure from the case closing is recorded by a sensor (e.g. pressure sensitive transducer) in the smart case 200. There may an indicator (e.g., LED light and/or array, electroluminescent display, electronic paper) on the smart case 200 to prompt the user to initiate a medication event. There may also be an indicator (e.g., light and/or array, electroluminescent display, electronic paper) on the smart case 200 to prompt the user with instructions regarding which specific medication to take, how many medication doses to take, or other information related to the medication dosage schedule. The smart case can additionally or alternatively include an auditory feedback, tactile feedback, or any other type of interface configured to provide a perceptible reminder and/or feedback to the user to consume a medication dose or to alert the user if a scheduled dose was missed.

In one embodiment, the strength of the feedback increases as the time and/or geographical location of the standard medication dosing window draws closer. For example, in one embodiment the smart case 200 can be paired with a mobile phone 102 to detect proximity of the user 108, and if a pre-defined degree of proximity was detected within or after the standard, i.e. recommended, medication dosing window, the feedback on the medication adherence system 100 would automatically engage to attempt to alert the user 108. The medication adherence system 100 may also have the functionality to not engage the feedback within the standard medication dosing window if the user 108 is not within a pre-defined degree of proximity. Other embodiments can have different methods for how to engage the user with feedback or stimuli based on dosing schedule, geographical location, and other important features.

The medication adherence system 100 includes a wireless communication module to transmit a medication event to the software application 104 wirelessly paired to the smart case 100, or to a wireless communication hub. If the medication adherence system 100 is unable to establish a wireless connection, the smart case 200 can store information regarding medication events in memory until a wireless connection is established. The smart case 200 may also include, but is not limited to, an internal clock, an accelerometer/gyroscope, and/or a GPS module to save additional relevant information related to the medication event. In one embodiment, the smart case 200 can use power from a local battery source to initiate a connection with a mobile phone 102 or wireless communication hub, and thereafter enter a "sleep" mode where the local computing device then powers the smart case 200 via direct or indirect means (e.g. inductive coupling) to extend the battery life of the aforementioned smart case 200.

In an alternative embodiment of the smart case 200, the dimensions of the case can be configured to match different shapes and sizes of medication packs 301, such as circular birth control packs.

In one embodiment, the smart case 200 may take the form of an outer sheath with a surface that receives a medication pack 301 that slides in and out of the sheath. The smart case detects when a medication dose is removed by detecting the location at which a medication dose and/or the medication pack crossed the threshold of the smart case (e.g. a grid). The sensors for detecting a medication event may include optical, electrical, mechanical, electromagnetic, capacitive, resistive, or piezo electric means. Sensors may be integrated together to improve the predictive accuracy of the medication adherence system, e.g. only events are recorded where large force is generated via piezo electric transducer, and optical coupling is interrupted by the rupture of a medication dose holder.

The description and specific examples herein are intended for purposes of illustration only and are not intended to limit the scope of the present disclosure. Therefore, the scope of the appended claims should not be limited by the specific examples set forth, but should be given the broadest interpretation consistent with the description as a whole.

What is claimed is:

1. A medication compliance case for receiving a medication pack having a plurality of medication dose holders and wirelessly communicating with an external device, said case comprising
 a base shell for removably receiving the medication pack;
 a lid attached to the shell and having a closed position where the medication pack is covered and open position where the medication dose holders on the medication pack are accessible by a user;
 a magnetic latch mechanism comprising a metal element on the lid and a metal element on the base shell, wherein at least one of the metal element on the base shell and the metal element on the shell is magnetic;
 a lid motion sensor configured to detect when the lid is moved between the closed position and the open position, wherein said lid motion sensor comprises a Hall Effect sensor configured to detect at least one of opening and closing of the latch mechanism;
 an inductive sensor on the base shell configured to detect when the medication pack is removed from the medication compliance case;
 circuitry comprising a processor and a wireless link, wherein the lid motion sensor and the inductive sensor are connected to the circuitry and the circuitry is configured to emit a signal via the wireless link to the external device when the lid is opened and when the medication pack is removed; and
 a power source connected to the circuitry.

2. A medication compliance case as in claim 1 wherein the lid is attached to the base by a hinge.

3. A medication compliance case as in claim 1 wherein the lid is slidably attached to the base and the lid motion sensor detects when the lid is slid to an open position.

4. A medication compliance case as in claim 1 wherein the circuitry is configured to power the inductive sensor only when the lid sensor indicates that the lid is open.

5. A medication compliance case as in claim 1 further comprising a dose holder sensor which detects opening of a single dose holder, wherein the dose holder sensor is connected to the circuitry and the circuitry is configured to emit a signal via the wireless link to the external device each time a dose holder is opened.

6. A medication compliance case as in claim 5 wherein the dose holder sensor comprises a capacitive, resistive, electromagnetic, optical, inductive, mechanical, acoustic, or image processing sensors.

7. A medication compliance case as in claim 5 wherein the circuitry is configured to power the dose holder sensor only when the lid motion sensor indicates that the lid is open.

8. A medication compliance case as in claim 1 further comprising a frame attached to the base for removably receiving the medication pack.

9. A medication compliance case as in claim 8 wherein the frame is attached to the base by an attachment mechanism that raises the frame and medication pack above an upper surface of the base when the lid is opened.

10. A medication compliance case as in claim 9 wherein the attachment mechanism comprises a spring hinge.

11. A method for facilitating compliance with a medication dosage schedule, the method comprising:
 providing a medication compliance case according to claim 1, said medication compliance case holding a medication pack comprising a plurality of individual medication dose holders:
 sensing, with a processor, the lid motion sensor on the medication compliance device when a user has opened the lid to gain access to individual medication dose holders on the medication pack;
 sensing, with the processor, the inductive sensor on the medication compliance device when a user has removed the medication pack from the medication compliance case; and.

12. A method as in claim 11, wherein the lid motion sensor is active at all times and the inductive sensor is energized to be in a sensing mode only after the lid motion sensor detects that the lid is open.

13. A method as in claim 11, furthermore comprising providing feedback to the medication user, if the user is determined to be in compliance.

14. A method as in claim 11, furthermore comprising providing feedback to the medication user, if the user is determined not to be in compliance.

15. A method as in claim 14, comprising feedback to the medication user that includes instructions on how to proceed if the user is determined not to be in compliance.

16. A method as in claim 15, comprising feedback to the medication user that includes information regarding a potential risk of pregnancy and instructions on how to minimize such risk, and wherein the medication is an oral contraceptive.

* * * * *